United States Patent
Triplett et al.

(10) Patent No.: US 7,762,992 B2
(45) Date of Patent: Jul. 27, 2010

(54) SAFETY NEEDLE WITH POSITIVE FLUSH

(75) Inventors: Daniel J. Triplett, Providence, UT (US); Kevin W. Sheetz, Sandy, UT (US); Eddie K. Burnside, Grantsville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 12/509,994

(22) Filed: Jul. 27, 2009

(65) Prior Publication Data

US 2009/0287159 A1 Nov. 19, 2009

Related U.S. Application Data

(62) Division of application No. 11/499,284, filed on Aug. 4, 2006, now Pat. No. 7,569,044, which is a division of application No. 10/648,969, filed on Aug. 27, 2003, now Pat. No. 7,097,637.

(51) Int. Cl.
*A61M 5/00* (2006.01)
(52) U.S. Cl. .................. 604/181; 604/164.02; 604/185; 604/195; 604/513
(58) Field of Classification Search ................ 604/110, 604/506, 513, 164.02, 164.06, 171, 185, 604/192, 195, 181
See application file for complete search history.

(56) References Cited

U.S. PATENT DOCUMENTS

| | | | |
|---|---|---|---|
| 3,957,048 A | 5/1976 | Jacobs |
| 4,464,178 A | 8/1984 | Dalton |
| 4,627,843 A | 12/1986 | Raines |
| 4,710,176 A | 12/1987 | Quick |
| 4,735,618 A | 4/1988 | Hagen |
| 4,743,231 A | 5/1988 | Kay et al. |
| 4,790,828 A | 12/1988 | Dombrowski et al. |
| 4,795,443 A | 1/1989 | Permenter et al. |
| 4,813,939 A | 3/1989 | Marcus |
| 4,826,490 A | 5/1989 | Byrne et al. |
| 4,850,977 A | 7/1989 | Bayless |

(Continued)

FOREIGN PATENT DOCUMENTS

WO WO-0204065 1/2002

(Continued)

OTHER PUBLICATIONS

Brochure, Specialized Health Products®, Incorporated © Copyright 2001, Revisions date: Nov. 2001, "LiftlLock™ Safety Infusion Set" pp. 1-7.

*Primary Examiner*—Kevin C. Sirmons
*Assistant Examiner*—Bhisma Mehta
(74) *Attorney, Agent, or Firm*—Rutan & Tucker, LLP

(57) ABSTRACT

A safety needle device and method of supplying fluid to a vascular access port is described. The device may include a base member, a handle member, and a compressible member positioned between the handle member and a compression plate. The compressible member is coupled to a proximal end of a needle. Following the delivery of fluid to a vascular access port, the needle is removed by moving the handle member away from the base member, which collapses the compressible member, flushing fluid into the vascular access port to substantially replace a volume of the needle.

15 Claims, 14 Drawing Sheets

U.S. PATENT DOCUMENTS

| | | | |
|---|---|---|---|
| 4,861,341 A | 8/1989 | Woodburn |
| 4,863,434 A | 9/1989 | Bayless |
| 4,863,435 A | 9/1989 | Sturman et al. |
| 4,863,436 A | 9/1989 | Glick |
| 4,886,503 A | 12/1989 | Miller |
| 4,887,998 A | 12/1989 | Martin et al. |
| 4,888,001 A | 12/1989 | Schoenberg |
| 4,898,589 A | 2/1990 | Dolgin et al. |
| 4,904,244 A | 2/1990 | Harsh et al. |
| 4,911,706 A | 3/1990 | Levitt |
| 4,950,250 A | 8/1990 | Haber et al. |
| 5,092,851 A | 3/1992 | Ragner |
| 5,108,379 A | 4/1992 | Dolgin et al. |
| 5,120,320 A | 6/1992 | Fayngold |
| 5,141,497 A | 8/1992 | Erskine |
| 5,147,319 A | 9/1992 | Ishikawa et al. |
| 5,242,417 A | 9/1993 | Paudler |
| 5,348,544 A | 9/1994 | Sweeney et al. |
| 5,370,624 A | 12/1994 | Edwards et al. |
| 5,423,766 A | 6/1995 | Di Cesare |
| 5,466,223 A | 11/1995 | Bressler et al. |
| 5,480,385 A | 1/1996 | Thorne et al. |
| 5,480,389 A | 1/1996 | McWha et al. |
| 5,487,734 A | 1/1996 | Thorne et al. |
| 5,531,704 A | 7/1996 | Knotek |
| 5,542,927 A | 8/1996 | Thorne et al. |
| 5,549,571 A | 8/1996 | Sak |
| 5,549,708 A | 8/1996 | Thorne et al. |
| 5,562,633 A | 10/1996 | Wozencroft et al. |
| 5,584,818 A | 12/1996 | Morrison |
| 5,616,135 A | 4/1997 | Thorne et al. |
| 5,656,031 A | 8/1997 | Thorne et al. |
| 5,672,161 A | 9/1997 | Allen et al. |
| 5,688,267 A | 11/1997 | Panescu et al. |
| 5,697,914 A | 12/1997 | Brimhall |
| 5,702,369 A | 12/1997 | Mercereau |
| 5,704,920 A | 1/1998 | Gyure |
| 5,718,688 A | 2/1998 | Wozencroft et al. |
| 5,735,827 A | 4/1998 | Adwers et al. |
| 5,738,665 A | 4/1998 | Caizza et al. |
| 5,743,886 A | 4/1998 | Lynn et al. |
| 5,755,694 A | 5/1998 | Camus et al. |
| 5,772,636 A | 6/1998 | Brimhall et al. |
| 5,772,643 A | 6/1998 | Howell et al. |
| 5,807,342 A | 9/1998 | Musgrave et al. |
| 5,810,780 A | 9/1998 | Brimhall et al. |
| 5,814,018 A | 9/1998 | Elson et al. |
| 5,823,997 A | 10/1998 | Thorne |
| 5,836,914 A | 11/1998 | Houghton |
| 5,836,917 A | 11/1998 | Thorne et al. |
| 5,879,337 A | 3/1999 | Kuracina et al. |
| 5,928,200 A | 7/1999 | Thorne et al. |
| 5,951,522 A | 9/1999 | Rosato et al. |
| 5,951,525 A | 9/1999 | Thorne et al. |
| 5,957,892 A | 9/1999 | Thorne |
| 5,980,488 A | 11/1999 | Thorne |
| 6,024,727 A | 2/2000 | Thorne et al. |
| 6,036,675 A | 3/2000 | Thorne et al. |
| 6,254,575 B1 | 7/2001 | Thorne, Jr. et al. |
| 6,261,259 B1 | 7/2001 | Bell |
| 6,280,420 B1 | 8/2001 | Ferguson et al. |
| 6,527,747 B2 | 3/2003 | Adams et al. |
| 6,824,530 B2 * | 11/2004 | Wagner et al. ............... 604/162 |
| 2001/0021827 A1 | 9/2001 | Ferguson et al. |
| 2001/0039401 A1 | 11/2001 | Ferguson et al. |
| 2002/0072716 A1 | 6/2002 | Barrus et al. |

FOREIGN PATENT DOCUMENTS

WO    WO-03035143    5/2003

* cited by examiner

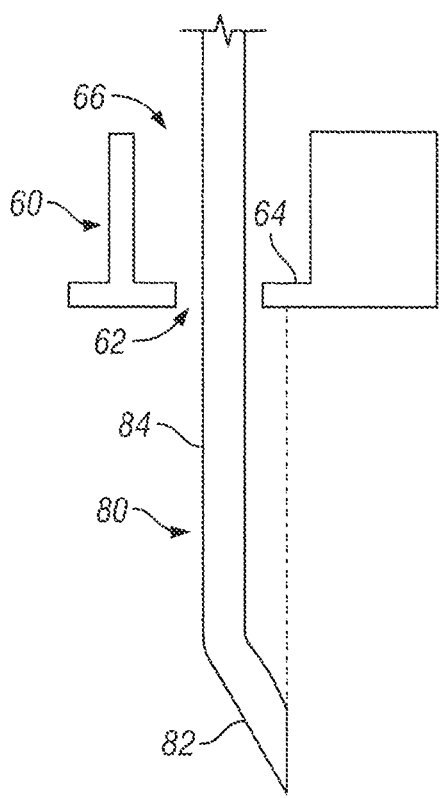
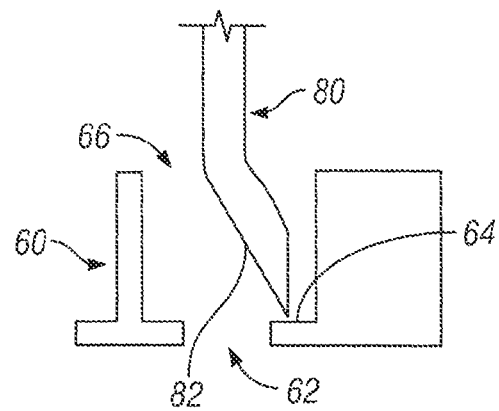
FIG. 5B
FIG. 5A

SAFETY NEEDLE WITH POSITIVE FLUSH

PRIORITY

This application is a divisional of U.S. patent application Ser. No. 11/499,284, filed Aug. 4, 2006, now U.S. Pat. No. 7,569,044, which is a divisional of U.S. patent application Ser. No. 10/648,969, filed Aug. 27, 2003, now U.S. Pat. No. 7,097,637, each of which is incorporated by reference in its entirety into this application.

BACKGROUND

The present invention relates generally to medical devices and more particularly to needle safety devices and positive flushing mechanisms.

Implantable vascular access systems are used extensively in the medical field to facilitate the performance of recurrent therapeutic tasks inside the body of a patient. Such vascular access systems generally include an implantable vascular access port attached to a vascular catheter. A typical vascular access port has a needle-impenetrable housing that encloses a fluid reservoir that is accessible from the exterior of the access port through a needle-penetrable elastomeric septum.

The entirety of the system, both the vascular access port and the catheter attached thereto, is implanted in the body of a patient. The distal tip of the catheter is disposed at a predetermined location where therapeutic activity is to be effected. Once the vascular access system is implanted, the tip of a hypodermic needle can then be employed selectively and repeatedly to access the fluid reservoir of the access port by penetrating the skin at the implantation site for the access port and then by being advanced through the septum of the access port itself.

While often times syringe-type devices are utilized for vascular access ports in acute or short-term situations, a special type of device is utilized for longer term infusion therapy. Such an infusion assembly device generally consists of a needle and wing assembly that lies flat against the skin in an insertion position, the needle having a proximal end attached to a wing assembly that is in angular relation to the needle shank, the angle being approximately 90°. As mentioned, when this longer term needle device is inserted into the vascular access port, it lies flat against the patient's skin and is adhered thereto as described, for example, in U.S. Pat. No. 4,710,176 to Quick.

With respect to the needle tip of the needle used in infusion assemblies for vascular access ports, a non-coring configuration is generally utilized due to repeated entry of the needle into the septum of the vascular access port. When the tip of a hypodermic or other traditional needle advances through the septum, coring occurs if any portion of the septum material is forced inside the shaft of the needle through the opening in the tip thereof. That portion of the septum material forced inside a needle in this process is in effect severed from the rest of the body of the septum material. Such septum coring produces small, detached particles of the septum that are likely to enter the fluid that is infused by the implanted vascular access system into the vascular system of the patient. These particles can obstruct fluid flow through the outlet stem of the vascular access port, or if escaping through the outlet stem of the vascular access port, can become trapped in the cardiovascular system of the patient.

In addition, septum coring produces small passageways through the body of a septum. On occasion these passageways extend entirely through the septum, from the exterior thereof to the fluid reservoir inside the vascular access port. The inwardly directed forces imposed on the installed septum by the housing of a vascular access port should initially urge the material of the body of the septum inwardly upon itself to close such passageways after the shaft of the needle is withdrawn therefrom. Nonetheless, continued coring eventually leads to various forms of septum failure that cannot be overcome by such inwardly directed forces. The material continuity of the septum is increasingly compromised, resulting in crumbled areas of the septum matrix. Eventually, leakage of fluid can be expected through the septum from the fluid reservoir in the vascular access port. Once such fluid escapes to the exterior of the vascular access port, necrosis will occur of the tissue surrounding the subcutaneous pocket in which the vascular access port is implanted, causing many undesirable consequences. Therefore, non-coring or Huber needles are preferably used in conjunction with infusion assemblies for vascular access ports. These needles, in contradistinction to the standard or traditional hypodermic needles pierce the septum like a knife, facilitating the resealing thereof so that the aforementioned problems are largely averted.

As with any needle-type device, there exists the problem of inadvertent needle sticks, which generally occur when the needle-type device is withdrawn from the patient prior to appropriate disposal thereof. Of course, inadvertent needle sticks introduce a variety of concerns due to unwanted transmission of blood from the patient to the medical practitioner. Inadvertent needle sticks can occur because of carelessness on the part of the medical practitioner or due to accidents in the handling of devices with exposed needle tips. With respect to Huber needles specifically, needle stick accidents can occur due to difficulty in removal as well. This difficulty results from the configuration of the Huber needle, which gets hooked into the port making it difficult to remove. Increased pulling force on behalf of the medical practitioner to dislodge the needle from the port results in less control over the tip of the needle when freed from the port, causing the inadvertent needle stick.

To address the inadvertent needle stick problem in winged infusion assemblies, such as those described herein, various safety devices have been designed to encase the needle after it is withdrawn from the port. One such safety device is described in U.S. Pat. No. 5,755,694 to Camus. Camus discloses a needle base disposed over a segment of the needle at its proximal end, comprising two generally flat wings made of flexible material with one hinge connecting each of the wings to the needle base. Upon removal of the needle from the patient, the wings flex against a moveable member that keeps them adjacent the needle until the needle is completely removed from the skin of a patient after which the wings surround the needle to prevent the tip from making contact outside of the needle base.

Another type of safety device is described in U.S. Pat. No. 5,951,522 to Rosato et al., in which the particular configuration of the Huber needle is also taken into account. Rosato et al. discloses a safety enclosure comprising a wing assembly mounted to the aft end of an angled Huber needle, the wing assembly having a configuration consisting of either a single integral member having a plurality of spaced apart fold lines which divide the member into a plurality of interconnected panels, or a pair of wing members mounted in a scissors-type arrangement. In each embodiment, when the medical practitioner removes the needle from the patient, the wing assembly closes around the needle and locks together, encasing it therein.

While many advancements have been made in the area of needle devices for use with vascular access ports, such as those described herein, there remains a heretofore unsolved problem related to removal of the needle device from the vascular access port. When the needle is inserted through the septum, it occupies a volume equal to the external dimensions thereof present in the fluid reservoir positioned underneath the septum. When the needle is removed from the vascular access port, the needle volume is evacuated without replacement, causing an equivalent volume of venous fluid to be drawn into the catheter tip at the distal end thereof. This infiltration of venous fluid is suspected to cause or contribute to thrombus formation at the catheter tip, which blocks the flow of fluid therethrough and results in early removal of the port and catheter from the patient. Early removal is costly, invasive, time-consuming, and otherwise extremely undesirable.

One solution to this problem of unwanted venous fluid being drawn into the catheter tip has been to implement a positive flushing technique as the needle is withdrawn. This technique generally consists of the medical practitioner inserting a syringe into the port and injecting a solution such as heparin while simultaneously withdrawing the needle. This technique, however, can be quite cumbersome and complicated and in fact may require more than one operator, as many of the infusion sets for use with vascular access ports require two hands to withdraw. For these reasons and others, it is known that a significant population of medical practitioners forego the practice of the described technique despite the adverse consequences that could result, as outlined herein. Therefore, it would be desirable to incorporate a flushing mechanism into a needle infusion set for use with a vascular access port so that flushing upon removal of the needle from the septum is assured.

In particular, it would be desirable to incorporate a positive flushing mechanism into various needle assemblies, one of which being an improved infusion needle assembly for use with a vascular access port that also provides a safety feature to prevent needle sticks.

BRIEF SUMMARY

Accordingly, a primary object of the present invention is to provide a needle assembly that incorporates a positive flushing mechanism. It is another object of the present invention to provide an improved needle assembly that will prevent accidental needle sticks upon the removal of the needle from the patient. It is yet another object of the present invention to provide an improved needle assembly that is configured to account for the geometry of a Huber needle. It is still another object of the present invention to provide a method of withdrawing a safety infusion set from a patient. It is a further object of the present invention to provide a method of positively flushing a vascular access port during withdrawal of the safety infusion set from a patient. Various other objectives and advantages of the present invention will become apparent to those skilled in the art as more detailed description is set forth below.

In accordance with the present invention, several embodiments are described, which may be improvements to prior art needle assemblies or may be novel infusion needle set embodiments heretofore undisclosed. As used herein, the following terms have the following meanings:

"Vascular access port" refers to a port having a needle-impenetrable housing enclosing a fluid reservoir that is accessible from the exterior of the port through a needle-penetrable elastomeric septum.

"Positive flush" refers to the action of a fluid being sent through a needle as the needle is being removed from a reservoir of a vascular access port or similar device so that the fluid replaces the volume that the needle occupies within the reservoir. It should be noted that the actual amount of fluid being sent through the needle will be greater than the volume of the needle in most cases.

In one embodiment of the present invention, a needle assembly is provided, including a needle, a body, and a base. The body is in the form of a collapsable male and female portion, where the collapsing action produces the positive flush following delivery of a drug or medicine to an implanted vascular access port. The base includes a contact patch that lies flat against the patient's skin for delivery of the drug or medicine and, which facilitates removal of the needle from the vascular access port. An arm and a hinge are attached to the contact patch, being respectively connected to the male and female portions of the body. When the needle assembly is moved from an insertion position to a protection position, the collapsing action of the body flushes fluid therefrom simultaneous to the needle exiting the vascular access port, creating a positive flush and preventing any negative pressures therein. The needle assembly contains a primary and secondary locking mechanism to ensure that accidental needle sticks are avoided.

In an alternate embodiment of the present invention, a winged assembly is provided, including a needle, a needle housing, and a collapsible reservoir. The needle housing has an upper and lower portion that are connected to one another. The upper portion houses the collapsible reservoir, which is adhered thereto in a way that allows complete and uniform collapse. The proximal end of the needle is attached to the front end of the upper portion and is fluidly connected to the collapsible reservoir. A connector is attached to the rear end of the upper portion, also in fluid communication with the reservoir, the connector being configured for attachment to an extension tubing set. The lower portion contains four connected panels, having locking mechanisms associated therewith to releasably lock the winged assembly in the insertion position and to permanently lock the winged assembly in the protection position. When the winged assembly is moved from an insertion position to a protection position, extensions on the lower portion of the needle housing press against the collapsible reservoir simultaneous to the needle exiting the vascular access port, expunging fluid therein through the needle to create a positive flush.

In another embodiment of the present invention, a needle assembly is provided, including a needle, a handle, a wing base, and a support structure. The handle has a left and right half which are connected together around a balloon extension that is connected to the proximal end of the needle and is in fluid communication therewith, and a compression plate that is connected to legs of the support structure. The support structure is bonded to the bottom of the wing base, the legs thereof fitting through holes in the wing base. The handle is movable with respect to the wing base and support structure for movement from an insertion position to a protection position. The balloon extension is trapped between the compression plate and handle so that movement of the handle upward results in compression of the balloon extension. As the balloon extension is compressed, the fluid contained therein is flushed through the needle as the needle exits a vascular access port to create a positive flush.

These and other embodiments, features, and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 5A is a close-up cross-sectional view of the needle housing of the needle assembly of FIG. 1 in the insertion position.

FIG. 5B is a close-up cross-sectional view of the needle housing of the needle assembly of FIG. 1 in the protection position.

DETAILED DESCRIPTION

The following detailed description should be read with reference to the drawings, in which like elements in different drawings are identically numbered. The drawings, which are not necessarily to scale, depict selected preferred embodiments and are not intended to limit the scope of the invention. In particular, although the examples provided herein are related to use of the described embodiments with an implanted vascular access port, it is contemplated that the positive flushing feature could be used with other medical devices to avert negative pressures upon the removal of needles or other medical equipment from a sealed system.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
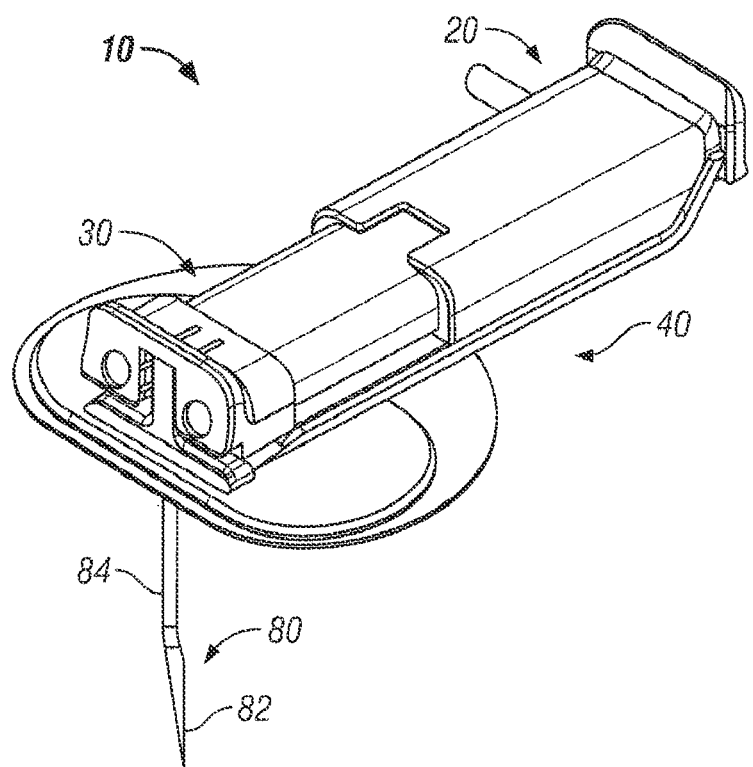
FIG. 1 is a perspective view of a needle assembly according to the present invention in the insertion position.

In a first embodiment of the present invention, a safety needle assembly with positive flushing mechanism 10 is shown in FIG. 1. The assembly 10 is shown in the insertion or use position, ready for insertion into the septum of an implanted vascular access port within a patient (not shown). The assembly 10 has three main components: a body, having a male portion 20 and a female portion 30, a base 40, and a needle 80. The male portion 20 is attachable to an extension tubing set for delivery of a fluid through the body to the needle 80, where it is dispensed into the vascular access port. The male portion 20 and female portion 30 are collapsible so that following delivery of the fluid to the vascular access port, the fluid within the body can be expunged as the needle is withdrawn from the vascular access port, creating a positive flush. The collapsible action of the body during withdrawal of the needle 80 occurs simultaneously with mechanical precision as will be explained in detail below. The body and base 40 in this embodiment are constructed of plastic, although certainly a number of different materials are possible, as one of skill in the art would appreciate. The needle 80 has a non-coring configuration, meaning that the tip 82 of the needle is angularly bent with respect to the longitudinal axis of the needle shank 84.

Figure 2:
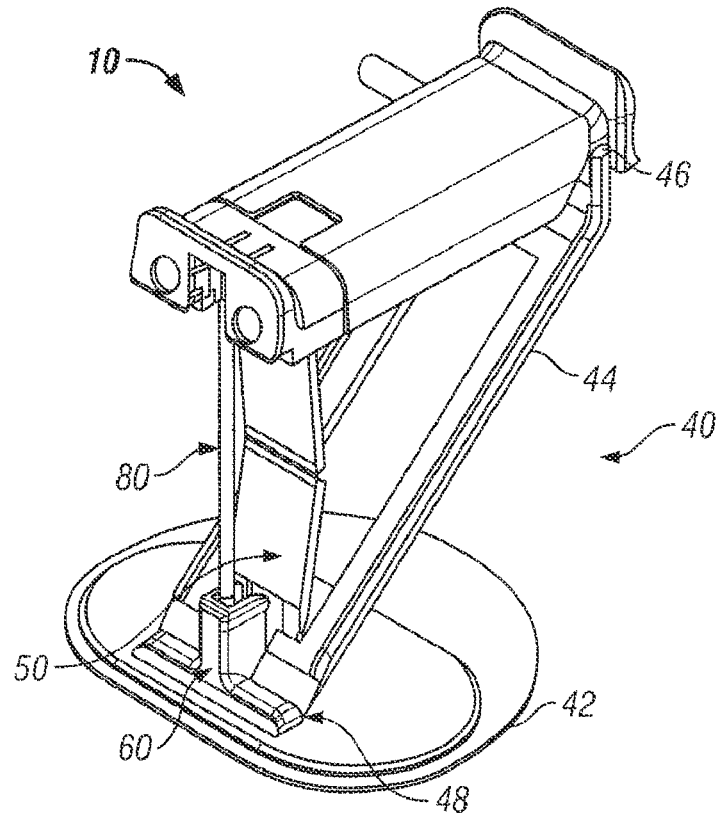
FIG. 2 is a perspective view of the needle assembly of FIG. 1 in the protection position.

FIG. 2 illustrates the assembly 10 in the protection or safe position, following withdrawal of the needle 80 from the vascular access port. From this view, the various elements of the base 40 can be seen. Base 40 includes a contact patch 42, which is a flat portion that rests against the skin of a patient and can be held thereto by a clinician as he begins withdrawal of the needle 80 from the vascular access port to maintain the position of the assembly 10 and allow for smooth mechanical interaction of the various components in providing the inventive positive flush. While the contact patch 42 is shown in a flat, rounded configuration, there are various other configurations that would equally be within the scope of the present invention, including configurations that take into account the particular area and contour of the body on which the assembly 10 is to be mounted so that the assembly 10 lies flush against the patient. In such an embodiment, the contact patch 42 would not have to be flat and instead could assume a variety of shapes as one of skill in the art should appreciate. It is noted that the use of a contact patch is advantageous in stabilizing the needle assembly 10 and facilitating smooth withdrawal of the needle, particularly in the event that the needle is stuck in the vascular access port or is otherwise difficult to remove.

Figure 3:
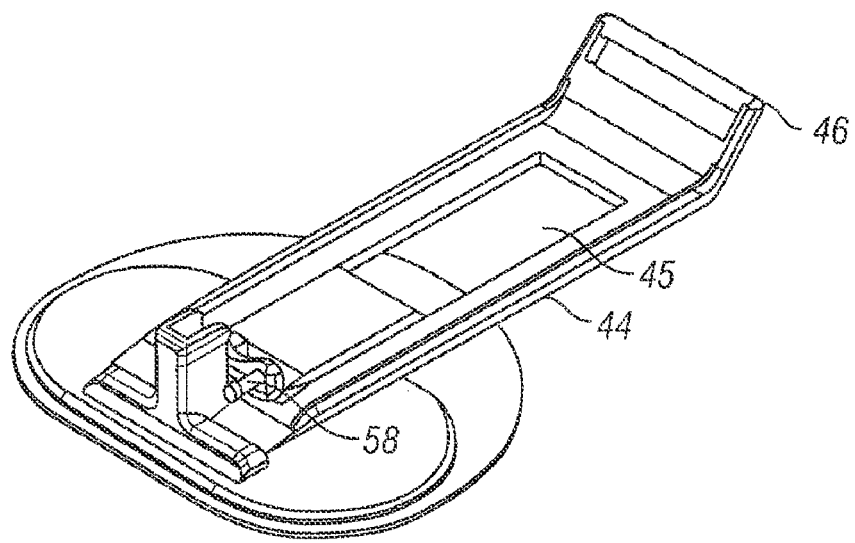
FIG. 3 is a perspective view of the base portion of the needle assembly of FIG. 1 in the insertion position of FIG. 1.
Figure 4:
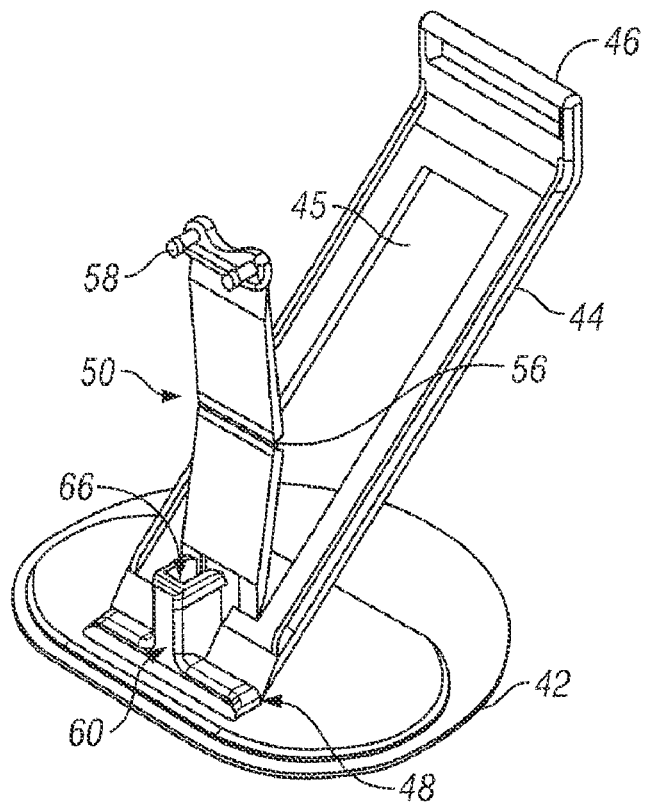
FIG. 4 is a perspective view of the base portion of the needle assembly of FIG. 1 in the protection position of FIG. 2.

Attached to the contact patch 42 is an arm 44. The arm 44 is either permanently connected to the contact patch 42 (through gluing, welding, etc.) at a first end 48 or is constructed as a single piece "living hinge" design. Opposite first end 48, the arm has a snap-fit interface 46 for unidirectional connection to the male portion 20 of the body. The unidirectional connection permits division between components (i.e., manufacturability) while ensuring that the safety feature of the design is not defeated. Integrally connected to the arm 44 and adjacent the first end 48 thereof is a hinge 50 for connection to the female portion 30 of the body to serve as a range of motion limit, which prevents over extension of the safety feature. The hinge 50 can be seen in more detail in FIGS. 3 and 4, showing the base 40 in the insertion position and protection position without the body for a clear view of the elements of the base 40 and their relative positions and movement in the two indicated positions of the assembly 10. Referring first to FIG. 3, the base 40 is shown in the insertion position, with arm 44 substantially flat against the contact patch 42 and hinge 50 folded within aperture 45 of arm 44. Pin interface 58 of the hinge 50 for connection to the female portion 30 is shown in its attached position.

FIG. 4 illustrates the base 40 in the protection position as both the arm 44 and the hinge 50 are moved in an upward direction with respect to the contact patch, which remains stationary against the skin of the patient. In this position, the full length of the hinge 50 can be seen, including an upper and lower portion connected by a hinge point 56. Also seen is a needle housing 60, positioned on the contact patch 42 abutting the first end 48 of the arm 44. The needle housing 60 has an open shaft 66 therethrough to permit passage of the needle 80. The needle housing 60 traps the needle therein when the assembly 10 is in the protection position, thereby providing a secondary locking mechanism to complement the primary locking mechanism provided by the body.

Referring to FIGS. 5A and 5B, one embodiment of needle housing 60 is provided. In this embodiment, the needle 80 passes through the needle housing shaft 66 and the distal opening 62 of the needle housing 60 as shown in FIG. 5A in the insertion position. The distal opening 62 of the needle housing 60 is smaller in diameter than the needle housing shaft 66, creating a ledge 64. Due to the non-coring configuration of needle 80 (where needle tip 82 is offset from needle shank 84) and the fact that the distal opening 62 is closely sized to the diameter of the needle shank 84, when the needle tip 82 passes through the distal opening 62 in a proximal direction, the tip 82 is deflected so that it may pass through the distal opening 62. As the needle 80 is drawn further in a proximal direction, the needle tip 82 enters the larger diameter needle shaft 66 where it returns to its initial axial position with respect to the distal opening 62 as shown in FIG. 5B in the protection position. This action results in the needle tip 82 being biased within the needle shaft 66, as movement in the distal direction is prevented by ledge 64. Variations to this embodiment include wedge or cone shaped features on the ledge 64 to further assist in preventing distal movement of the needle tip 82 through the distal opening 62. Other embodiments which would be apparent to one of skill in the art are also possible, depending on the shape and size of the needle.

Figure 6:
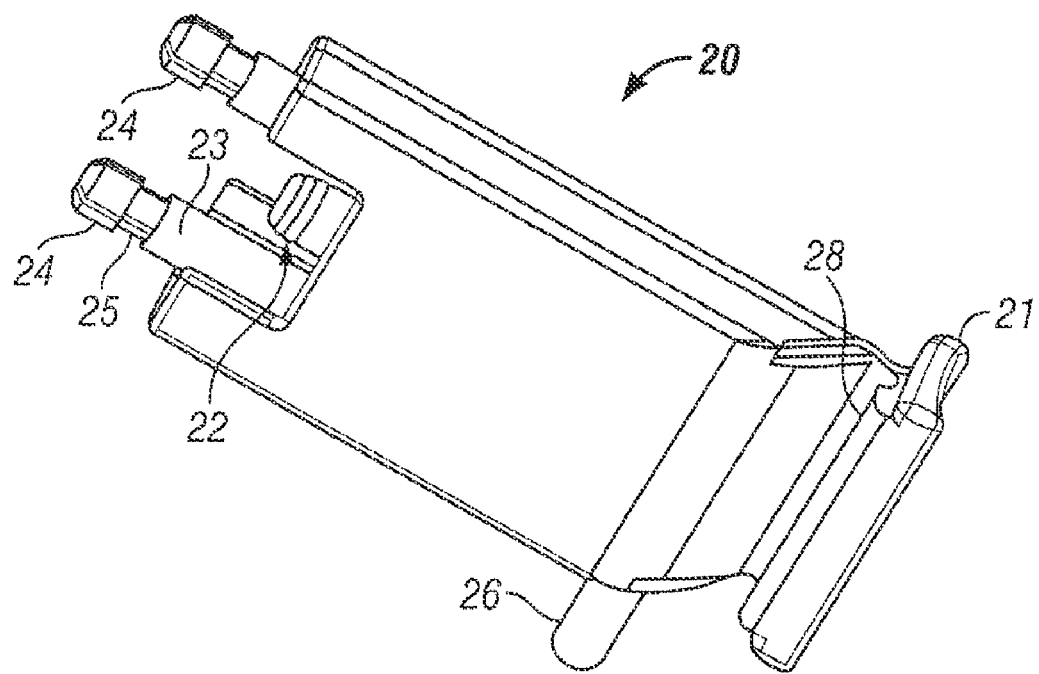
FIG. 6 is a bottom perspective view of the male portion of the body of the needle assembly of FIG. 1.
Figure 7:
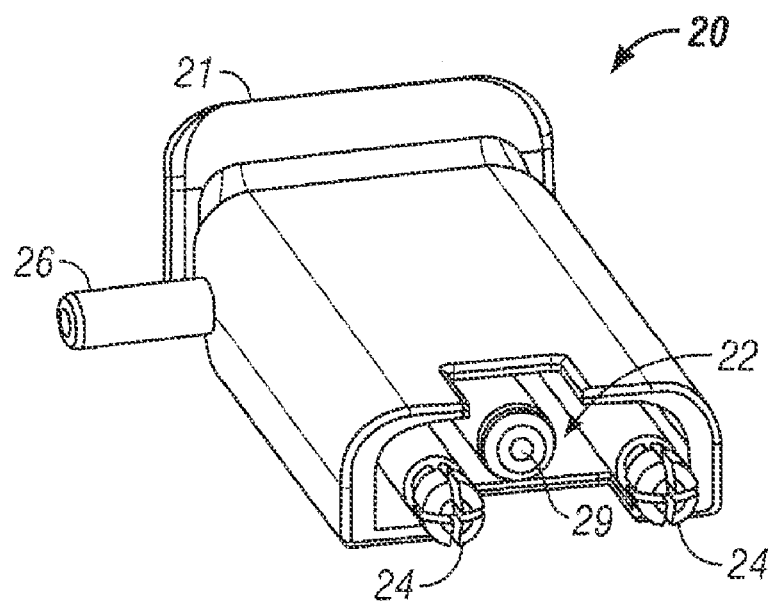
FIG. 7 is a top perspective view of the male portion of the body of the needle assembly of FIG. 1.

Referring now to FIGS. 6-9, the male portion 20 and the female portion 30 of the body are shown separately. In FIGS. 6 and 7, the male portion 20 is shown from a bottom (FIG. 6) and a top (FIG. 7) viewpoint. The male portion 20 has an extension leg tubing connector 26, a plunger 22 and two guide pins 23. The guide pins 23 are positioned on each side of the plunger 22 and contain at their distal end knobs 24 that act as a closure locking mechanism when received in recesses within the female portion 30. The knobs 24 have an expanded and a contracted diameter, which is created as shown in FIG. 7 by having four sections separated at their distal end, but joined at their proximal end at neck 25. Thus, with no radial pressure exerted thereon, the knobs 24 assume an expanded diameter approximately equivalent to the diameter of the guide pins 23.

However, under the force of radial pressure, for example exerted by a narrowing diameter, the four sections press together and thereby assume a contracted diameter that is smaller than the expanded diameter. Of course, the knobs 24 could be configured in other ways as one of skill in the art should appreciate, which would also impart an expanded and contracted diameter thereto based on the presence of an outside radial force. It is important to note that the sectioned distal end of the knobs 24 are rounded and tapered while their proximal end connected to the necks 25 is not. This configuration in conjunction with that of the proximal end of the female portion 30 produces the primary locking mechanism of this embodiment as explained in more detail below.

From the bottom view in FIG. 6, a snap groove 28 can be seen, which is configured to receive the snap-fit interface 46 of the arm 44. From the top view in FIG. 7, fluid passage opening 29 can be seen through the distal end of the plunger 22, where fluid flows to the female portion 30. The plunger 22 has an O-ring around its distal end to provide leak-resistance. Fluid passage 27 fluidly connects fluid passage opening 29 with an opening in the extension leg tubing connector 26 (see FIG. 10). In both views, a finger rest 21 can be seen on the proximal end of the male portion 20 to facilitate manual collapse of the male portion 20 into the female portion 30 by the clinician.

Figure 8:
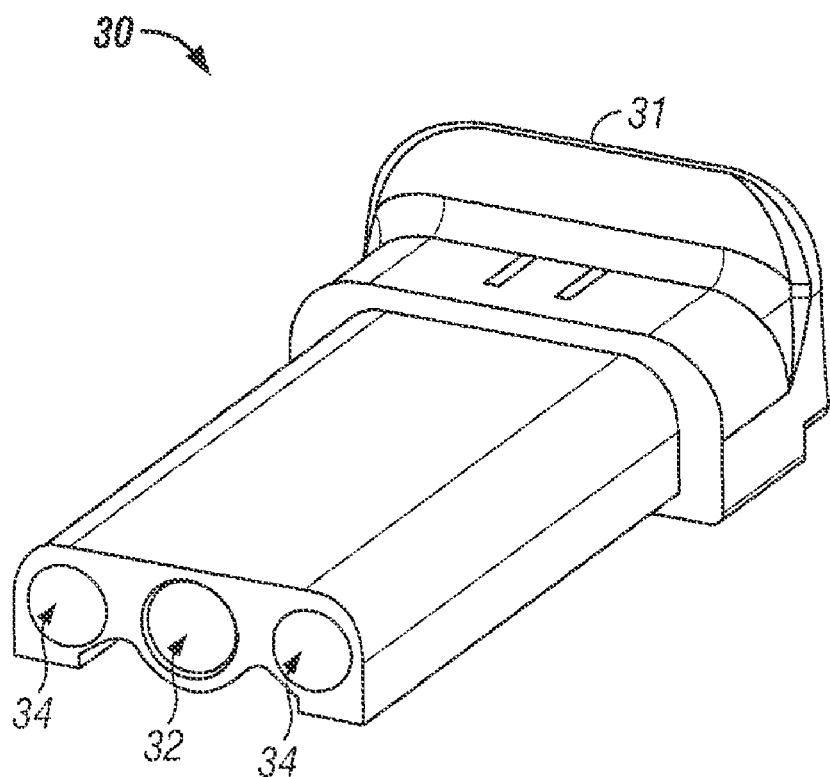
FIG. 8 is a perspective view of the proximal end of the female portion of the body of the needle assembly of FIG. 1.
Figure 9:
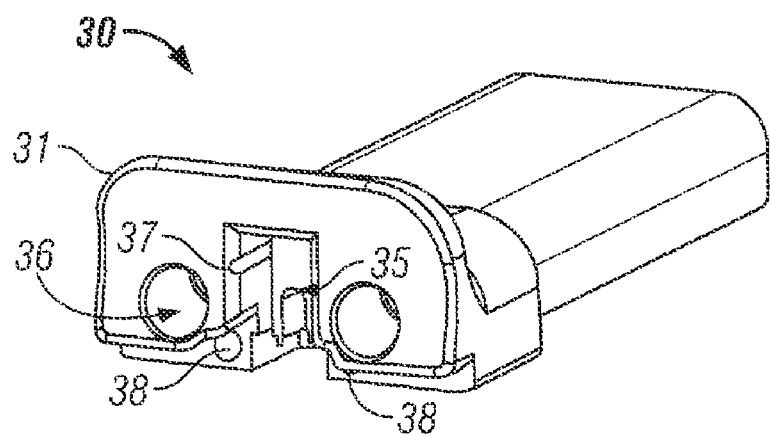
FIG. 9 is a perspective view of the distal end of the female portion of the body of the needle assembly of FIG. 1.

In FIGS. 8 and 9, the female portion 30 is shown from a proximal (FIG. 8) and a distal (FIG. 9) viewpoint. The female portion 30 contains a plunger receptacle 32 and guide pin receptacles 34, sized to slidingly receive the plunger 22 and guide pins 23 of the male portion 20 through a proximal end thereof. At a distal end of the female portion 30, a finger rest 31 is positioned, similar to finger rest 21 of the male portion 20, to facilitate collapse. From the distal viewpoint, locking chambers 36 can be seen that are configured to receive the knobs 24 of the guide pins 23 so that subsequent movement of the guide pins 23 is substantially prevented. The locking chambers 36 have a diameter equivalent to the guide pin receptacles 34, but include a narrowed region at the proximal end thereof to force the knobs 24 of the male portion 20 into their contracted diameter. After the knobs 24 move distal to the narrowed region and into the locking chambers 36, the knobs 24 resume their expanded diameter (due to the removal of pressure thereon) and are thereby "trapped" in the locking chamber as the narrowed region prevents proximal movement thereof due to the non-tapered configuration of the proximal end of the knobs 24.

Also shown in FIG. 9 is a needle mounting region 35, where a proximal end of the needle 86 (see FIG. 12) is held, and which enables fluid connection of the proximal end of the needle 86 to the plunger receptacle 32. While the mounting region 35 is shown as an arched area sized to frictionally hold the proximal end of the needle 86, which is angularly positioned relative to the needle shank 84, certainly many other configurations are possible, depending on the size and type of needle employed, which would equally be within the scope of the present invention. A mechanical interlock 37 is positioned on the proximal end of the female portion 30 for releasable connection to a recess on the base 40. The interlock 37 snaps into place when the assembly 10 is in the insertion position to prevent accidental movement of the assembly 10 during fluid delivery to a vascular access port. When it is desired to move the assembly into the protection position, the interlock 37 can be manually moved out of the recess. Of course, it should be appreciated that numerous types of releasable mechanisms would equally be desirable and are therefore contemplated to be within the scope of the present invention, including an embodiment wherein the recess was positioned on the female portion 30 and the mechanical interlock was positioned on the base 40. Pin interface receptacles 38 connect to the pin interface 58 of the hinge 50.

Figure 10:
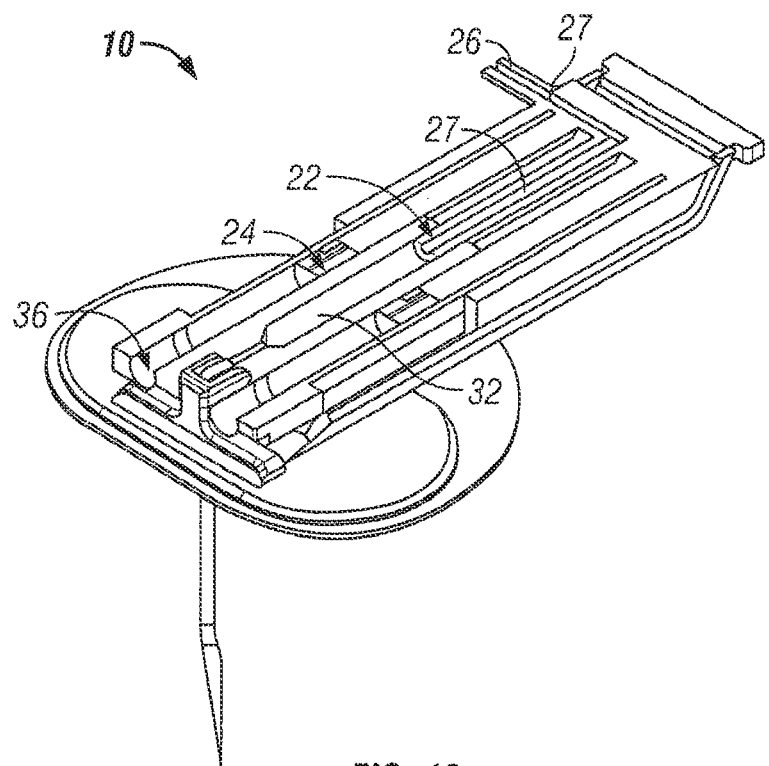
FIG. 10 is a top cross-sectional view of the needle assembly of FIG. 1 in the insertion position of FIG. 1.
Figure 11:
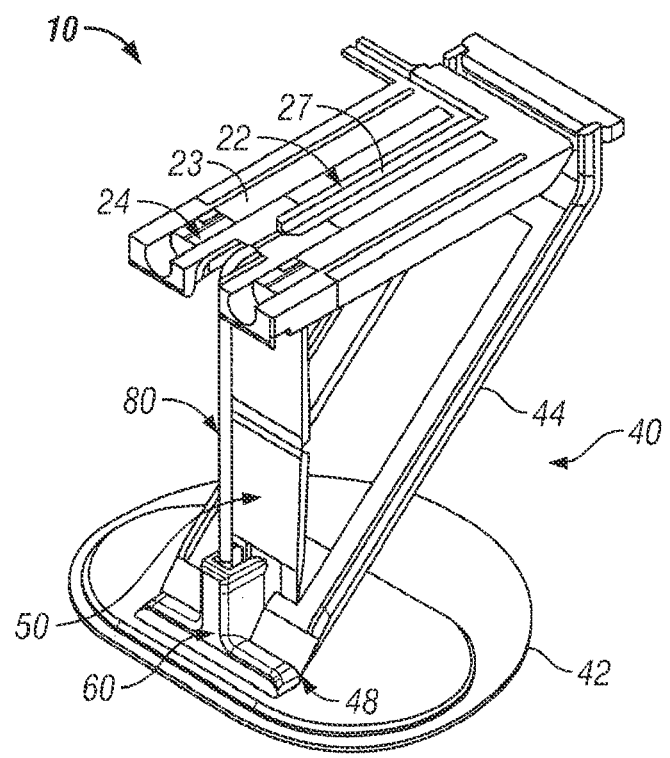
FIG. 11 is a top cross-sectional view of the needle assembly of FIG. 1 in the protection position of FIG. 2.

Turning now to FIGS. 10-11, the assembly 10 is shown in the insertion and protection positions with the body shown in cross-section to illustrate the action of the plunger 22 and the guide pins 23. Initially, in the insertion position, the male portion 20 is in an uncollapsed state with respect to the female portion 30 so that fluid passing through the extension leg tubing 26, into the fluid passage 27 and through the fluid passage opening 29 collects in the plunger receptacle 32 before flowing into the proximal end of the needle 86. As the assembly 10 is moved from the insertion position to the protection position, the plunger 22 and guide pins 23 of the male portion 20 are moved through the respective receptacles 32 and 34 of the female portion 30 as shown in FIG. 11. As explained above, when the knobs 24 on the distal ends of the guide pins 23 pass over the narrowed region of the locking chambers 36, the knobs 24 are prevented from moving proximally back into the guide pin receptacles 34, thereby providing a primary locking mechanism for the assembly 10.

Figure 12:
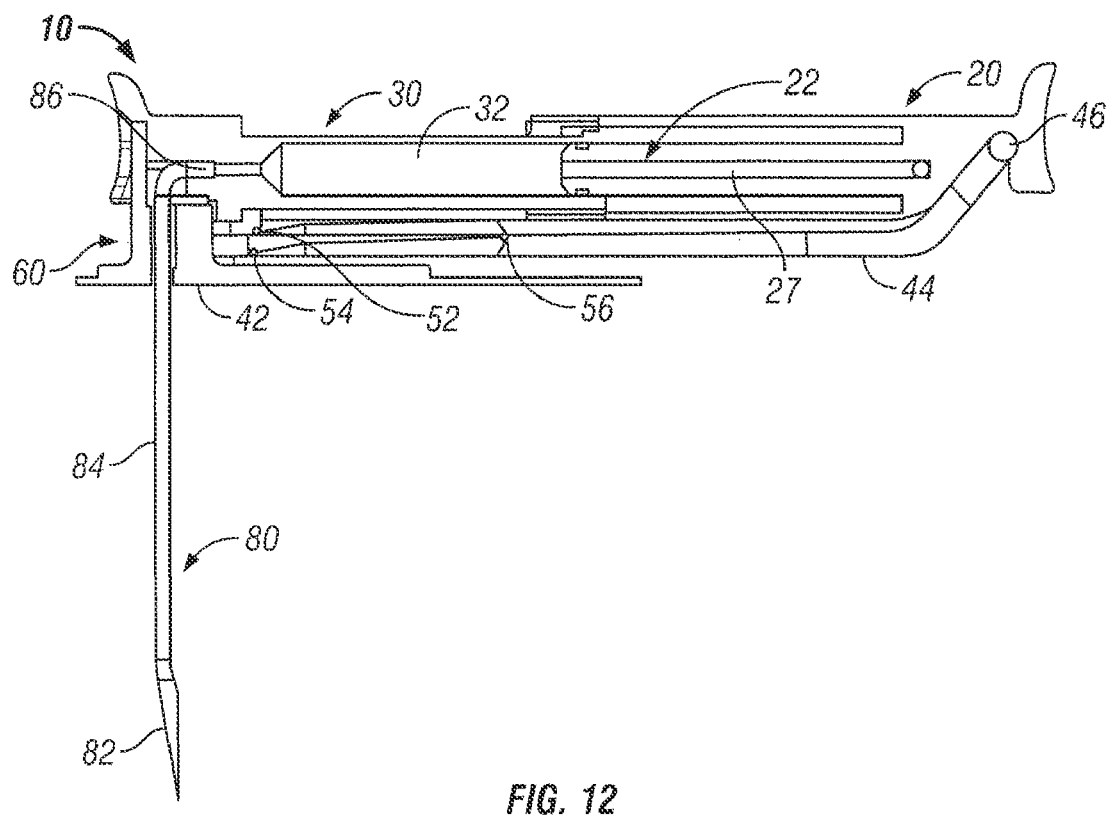
FIG. 12 is a side cross-sectional view of the needle assembly of FIG. 1 in the insertion position of FIG. 1.
Figure 13:
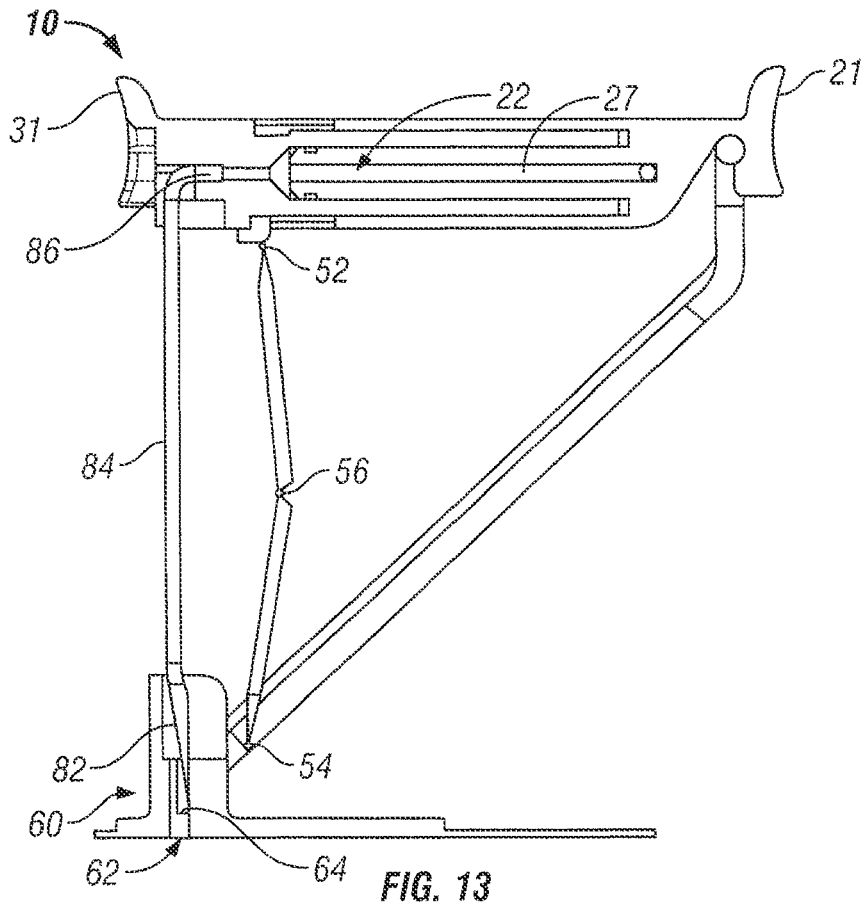
FIG. 13 is a side cross-sectional view of the needle assembly of FIG. 1 in the protection position of FIG. 2.

A use of the assembly 10 will be explained with reference to FIGS. 12 and 13, which show a side cross-sectional view of the assembly 10. The fully assembled assembly 10 is prepared for insertion into a vascular access port by first removing a protective sleeve over the needle (not shown). The exact location of the vascular access port and, in particular, the septum through which the needle of the assembly 10 is to be placed is identified by the clinician and by grasping the assembly 10 on either side thereof in the insertion position, the needle is pressed through the patient's skin and into the septum of the vascular access port. At this time, the contact patch 42 should be flat against the patient's skin and optionally can be secured thereto by utilizing tape or other adhesive. Extension leg tubing, which has previously been connected to the extension leg tubing connector 26 (or alternatively is attached following securing the lower portion to the patient's skin), is attached to a fluid source, which pumps fluid in the form of a drug or medicine through the extension leg tubing, into the fluid passage 27, through the plunger receptacle 32 and into the proximal end of the needle 86, through the needle 80 and into the vascular access port (not shown).

When fluid delivery has been completed, the clinician clamps the extension leg tubing, removes the tape or adhesive (if any), unlocks the mechanical interlock 37 from the recess in the base 40, places the fingers of one hand on the contact patch 42 and with the second hand squeezes the male portion 20 and female portion 30 together, utilizing respective finger rests 21 and 31. By securing the needle assembly 10 with one hand in contact with the contact patch, stability of the assembly 10 is ensured, which is particularly useful should the needle 80 become stuck or otherwise prove difficult to remove from the vascular access port. As mentioned above, this occurrence often times results in accidental needle sticks, which are prevented through the stable configuration of the described embodiment.

The squeezing together of the body causes simultaneous action in separate parts of the assembly 10. With respect to the base 40, as the male portion 20 of the body moves toward the female portion 30, the arm 44 is forced in an upward direction, which in turn carries the body upward, which moves the needle up and out of the vascular access port. Hinge points 52 and 54, at opposing ends of hinge 50, permit the hinge to open as the arm 44 moves. With respect to the fluid in the body, as the male portion 20 of the body moves toward the female portion 30, the plunger 22 expunges the fluid within the plunger receptacle 32 through the needle 80 as the needle is moving out of the vascular access port. This action creates a positive flush whereby the volume of fluid being expunged simultaneous replaces the volume of the needle in the reservoir of the vascular access port so that a negative pressure in the vascular access port is averted. Ideally, the volume of the infusion fluid contained in the body would be greater than the volume of the needle so that the infusion volume to the port can be manipulated by changing the geometry of the arm 44. Also, typically the fluid flow rate from the body during the positive flushing action is greater than the normal fluid flow rate through the assembly in the insertion position.

With respect to the body, the squeezing together of the male portion 20 and the female portion 30 eventually causes the knobs 24 on the distal ends of the guide pins 23 to move into the locking chambers 36 thereby preventing further relative movement of the male and female portions. At the same time, the needle tip 82 passes through the distal opening 62 and into the needle housing shaft 66 where it is biased therein, prevented from distal movement by ledge 64. Thus, in the protection position shown in FIG. 13, the assembly 10 is held in place by both a primary and secondary locking mechanism.

Figure 14:
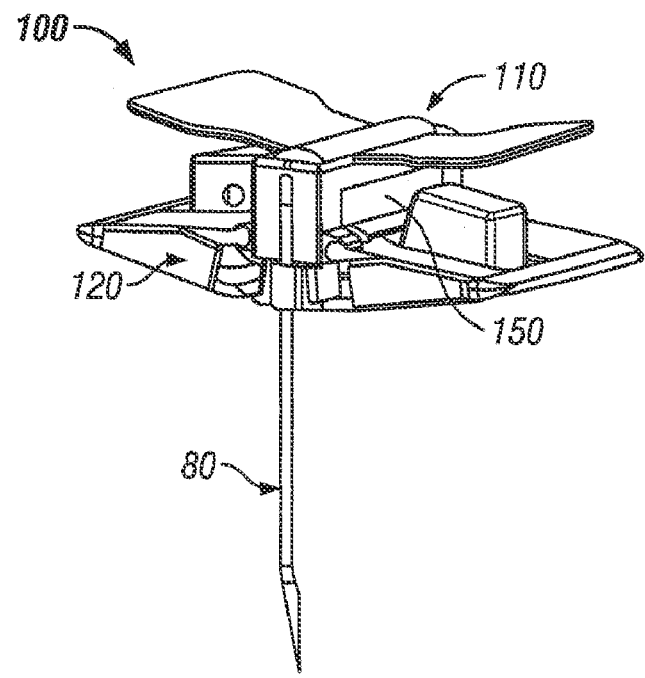
FIG. 14 is a perspective view of an alternate embodiment of the needle assembly of the present invention in the insertion position.
Figure 15:
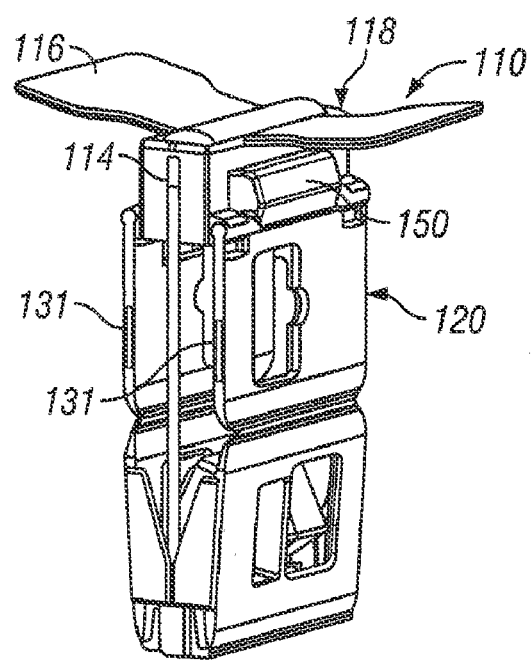
FIG. 15 is a perspective view of the needle assembly of FIG. 14 in the protection position.
Figure 16:
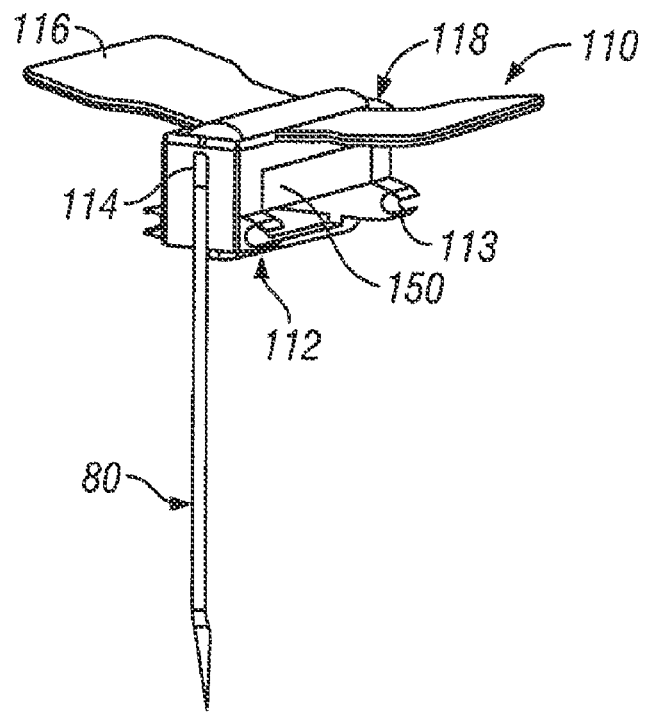
FIG. 16 is a perspective view of the upper portion of the needle assembly of FIG. 14 with an attached collapsible reservoir.

FIGS. 14-17 illustrate another embodiment of the present invention. Winged assembly 100 contains three primary components: a needle 80, a needle housing, having an upper portion 110 and a lower portion 120, and a collapsible reservoir 150. The winged assembly 100 is shown in FIG. 14 in the insertion position and in FIG. 15 in the protection position. Referring to FIG. 16, the upper portion 110 of the housing is shown without the lower portion 120 attached. The needle 80 is attached to the front 114 of the upper portion through an opening or groove therein with the use of adhesives, friction fit, mechanical means or some combination thereof. Needle 80 may or may not have a proximal end which is angularly positioned with respect to the shank thereof. The proximal end of the needle is fluidly connected to the collapsible reservoir 150, which is disposed within the upper portion 110 of the housing. The collapsible reservoir 150 is configured to be collapsible in the presence of externally exerted force and is so positioned within the upper portion 110 of the housing. In particular, the collapsible reservoir 150 is adhered to only a single horizontal surface of the upper portion 110 so that the vertical surfaces of the collapsible reservoir are allowed to collapse in a uniform manner.

At the rear of the upper portion 110, a connector 118 is attached to enable connection to an extension tubing, the connector being in fluid communication with the collapsible reservoir 150. Across the top region of the upper portion 110, opposing wings 116 span to facilitate grasping and movement of the winged assembly 100. At the base of the upper portion 110, below the attached collapsible reservoir 150, a portion containing four grooves 113 is positioned, which permit a snap-fit of the lower portion 120 therein, positive locking the lower portion 120 to the upper portion 110. Attached to the bottom of the upper portion 110 is a stiffening rib 112, which acts to provide structural support to the winged assembly 100 and which releasably locks the winged assembly 100 in the insertion position by snapping into grooves 142 in the lower portion 120 (see FIG. 17).

Figure 17:
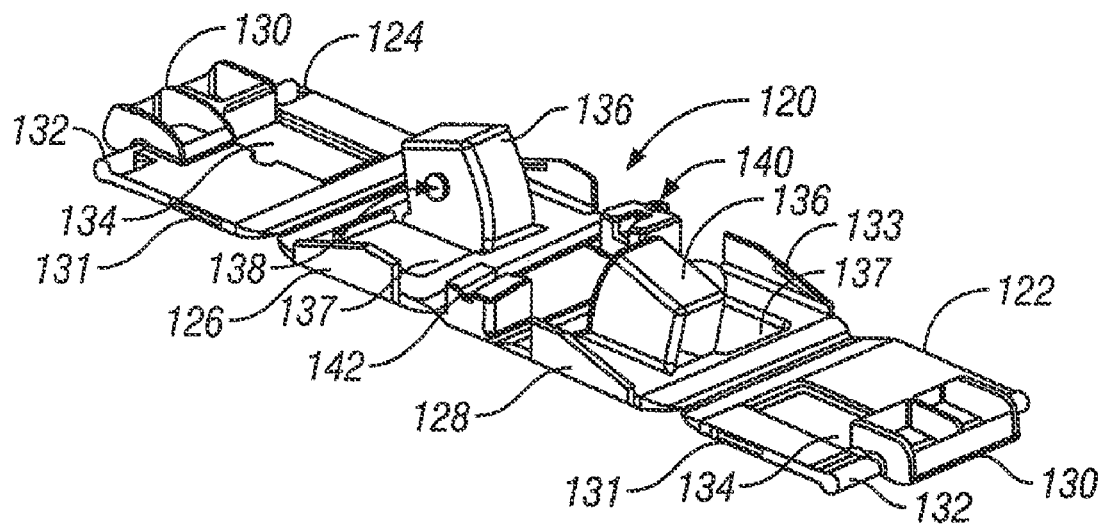
FIG. 17 is a view of the lower portion of the needle assembly of FIG. 14.
Figure 18:
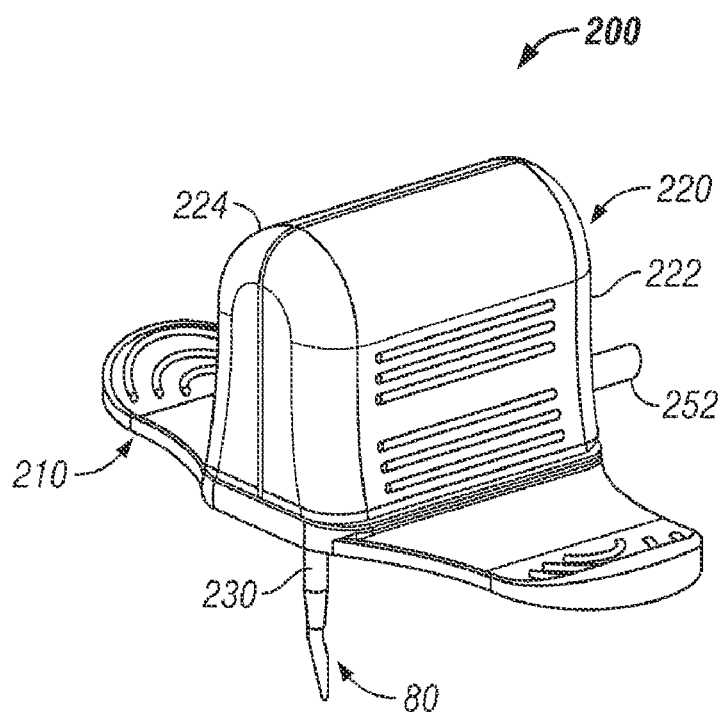
FIG. 18 is a perspective view of an alternate embodiment of the needle assembly of the present invention.
Figure 19:
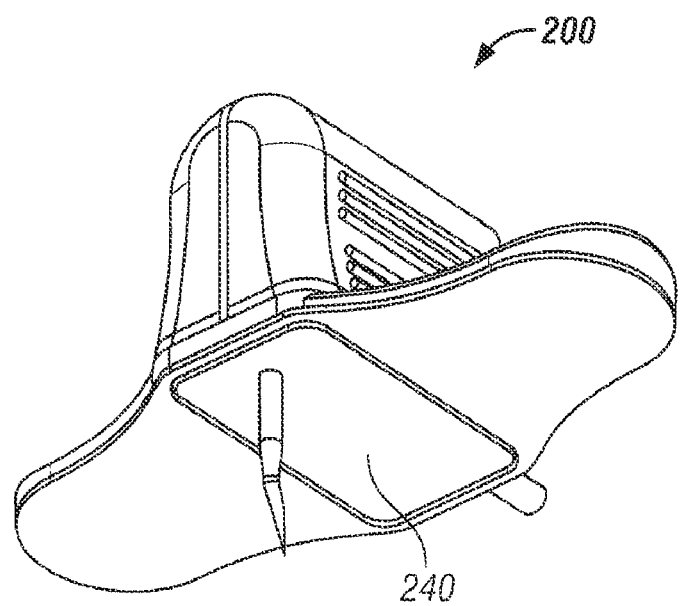
FIG. 19 is a bottom view of the needle assembly of FIG. 18.

Referring now to FIG. 17, the lower portion 120 is shown in isolation. The lower portion contains four panels that function through the use of living hinges therebetween. The four panels are really two panels that mirror each other, separated by a needle housing 140 and grooves 142 that interlock with the stiffening rib 112. The outer panels 122, 124 contain rods 132 that snap-fit within the grooves 113. Between the rods 132 are extensions 130, which press against the collapsible reservoir 150 as the winged assembly moves from an insertion position to a protection position, thereby collapsing the collapsible reservoir 150 and expunging the fluid therefrom. Below the extensions are windows 134 that align with protrusions 136 on adjacent inner panels 126, 128. On the sides of the outer panels 122, 124 are recesses 131, which are sized to receive locking sections 133 on the adjacent inner panels 126, 128 to releasably lock the winged assembly 100 in the insertion position.

In a separate locking mechanism, the protrusions 136 of the inner panels 126, 128 mate with one another in the protection position through the complementary button/detent thereon (FIG. 17 shows button 138 on protrusion 136, whereas FIG. 14 reveals the detent on the opposing protrusion 136) to permanently lock the winged assembly 100 in the protection position. Positioned adjacent the protrusions 136 are apertures 137 to allow full movement of the opposing protrusion 136 as the winged assembly 100 is moved into the protection position. While the protrusions 136 are illustrated as being offset from one another for mating purposes, it is envisioned that alternate embodiments would have other types of interlocking mechanisms that were not so offset and rather provided a positive locking feature by snapping together or otherwise permanently locking. Between the inner panels 126, 128 is a needle housing 140 that operates similarly to the needle housing 60 as explained above to prevent movement of the needle in a distal direction once the needle tip has passed into the needle shaft and is biased to its normal position.

Referring back to FIGS. 14 and 15, the operation of the winged assembly 100 is initiated by the clinician by removing a protective needle sheath (not shown) from the needle and grasping the wings 116 with one hand as the winged assembly 100 is locked in the insertion position (FIG. 14). The clinician squeezes the wings 116 together to grip the winged assembly 100 and presses the needle 80 into a patient's skin and into an implanted vascular access port. The inner panels 126, 128 of the lower portion 120, lying substantially flat against the patient's skin, can then be secured thereto for delivery of the fluid by applying tape or other type of adhesive to the lower portion 120 (for example, taping over the outer panels 122, 124). An extension tubing set, previously attached to the connector at the rear 114 of the upper portion 110 (or alternatively attached following securing the lower portion to the patient's skin), is itself connected to a fluid source, which pumps fluid through the connector, into the collapsible reservoir 150, through the needle 80 and into the vascular access port.

When delivery of the fluid is completed, the extension tubing is clamped and the tape or adhesive (if any) is removed. The clinician with one hand squeezes the lower portion 120 together, causing the locking sections 133 to disengage from the recesses 131 and the inner panels 126, 128 to align longitudinally with the outer panels 122, 124 as shown in FIG. 15. As the panels straighten with respect to one another, the needle is withdrawn from the vascular access port. It is noted that this configuration prevents accidental needle sticks due to the fact that the needle is never exposed outside of the body. As soon as the needle exits the skin, it is enveloped by the lower portion 120.

Simultaneously to the needle withdrawal, the extensions 130 on the outer panels 122, 124 press into the collapsible reservoir 150 causing it to collapse and expunge fluid therein through the needle 80 and into the vascular access port as the needle moves outward. This simultaneous action produces a positive flush whereby the volume of fluid being expunged simultaneous replaces the volume of the needle in the reservoir of the vascular access port so that a negative pressure in the vascular access port is averted. As the panels straighten, the protrusions 136 press together engaging the complimentary button/detent 138 positively and permanently locking the panels together. At the same time, the needle tip 82 passes through a distal opening of the needle housing 140 and into a needle housing shaft where it is biased therein, prevented from distal movement by a ledge. Thus, in the protection position shown in FIG. 15, the winged assembly 100 is held in place by both a primary and secondary locking mechanism.

Figure 20:
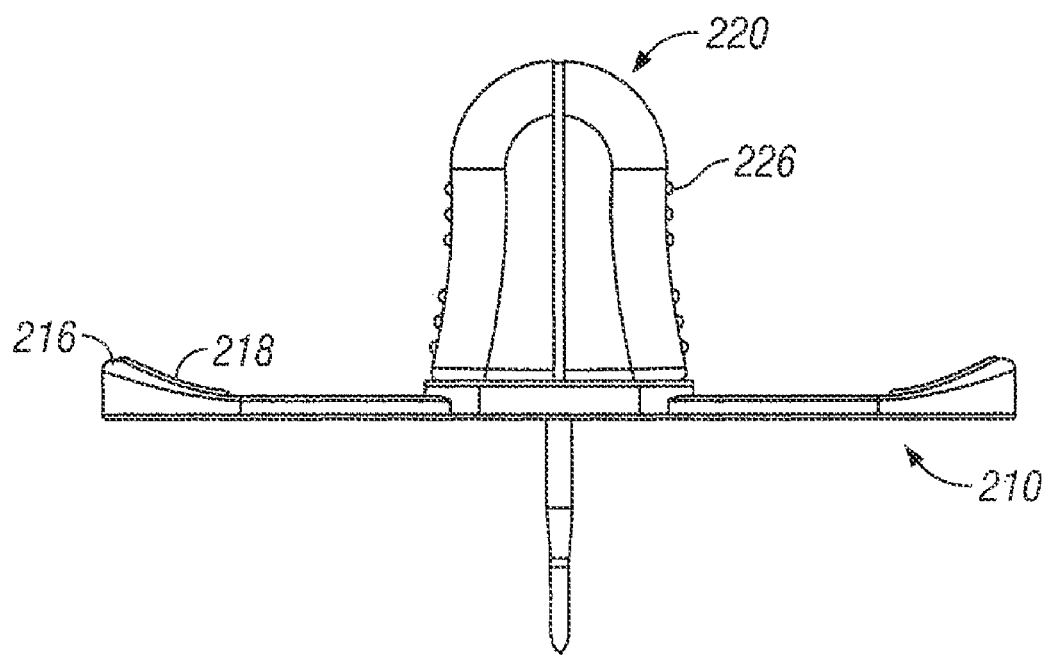
FIG. 20 is a front view of the needle assembly of FIG. 18.
Figure 21:
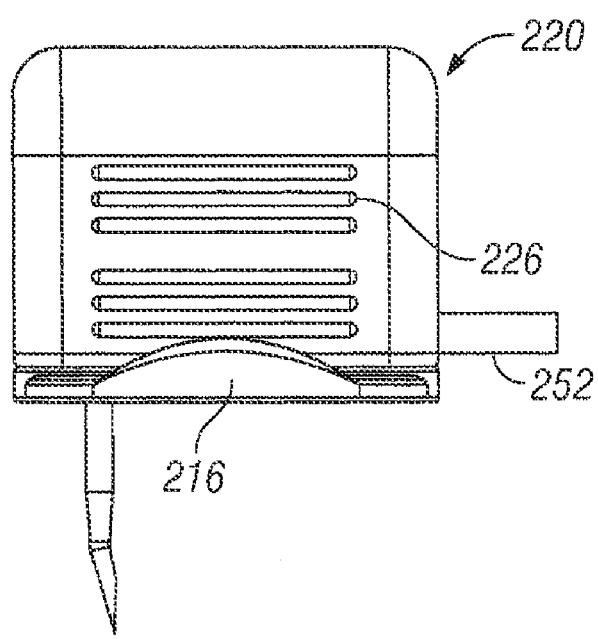
FIG. 21 is a side view of the needle assembly of FIG. 18.

In another embodiment of the present invention, illustrated by FIGS. 18-24, a balloon and compression plate combination acts as a mechanism by which a positive flush is created. Referring to FIGS. 18-21, various views of a needle assembly 200 are illustrated. Needle assembly 200 includes a wing base or base member 210 onto which is mounted a handle 220, having separate left 222 and right 224 halves that interlock with one another when assembled. The wing base 210 includes first and second wing sections extending from opposite sides of a central section. Below the wing base 210 is a support structure 240, which has an opening 248 for needle 80. As best seen in FIG. 20, both the handle 220 and the first and second wing sections of the wing base 210 have contoured surfaces for finger placements along with respective ridges 226 and 218 for gripping. The contoured surface 216 of wing base 210 comprises a raised portion at each opposing end. These features provide ease of use and protect against slippage. Needle 80 is fluidly connected to tail 252, which is configured for connection to extension leg tubing and to a fluid source (not shown).

Figure 22:
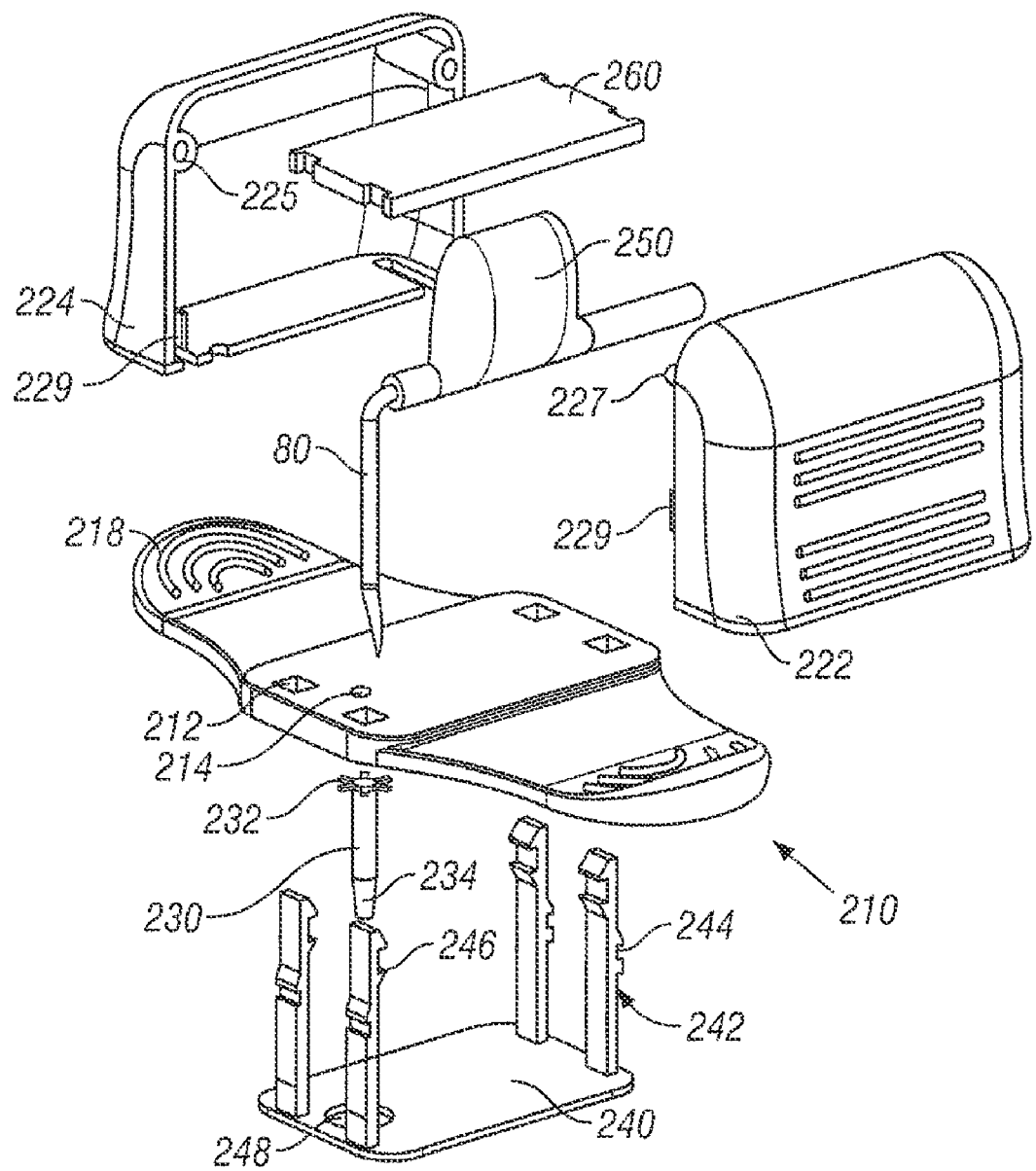
FIG. 22 is an exploded view of the needle assembly of FIG. 18.

An exploded view of needle assembly 200 is illustrated in FIG. 22, showing the separate parts prior to assembly. The support structure 240 is assembled through the bottom of the wing base 210 through four openings 212, each of which accommodates a leg 242 of the support structure, the legs 242 extending at about a 90 degree angle from the support structure. The plurality of legs 242 angularly extend from the central section and are each configured with a first notched section 244 and a second notched section 246, which serve different purposes as will be explained more fully below. Support structure 240 and wing base 210 each contain an opening 248, 214 that are aligned for receiving a protection sleeve 230 and the needle 80. The protection sleeve 230 is made of a material thick and/or tough enough so that the needle 80 cannot penetrate through in the protection position, such as nylon, though certainly a number of materials are certainly possible. The protection sleeve 230 has a proximal portion 232, having an increased radius for bonding between the support structure 240 and the wing base 210. The protection sleeve 230 also has a distal portion 234 with a tapered configuration for ease of insertion within the body of a patient.

The left 222 and right 224 halves of handle 220 snap together on top of the wing base 210, enclosing therein a proximal end 86 of the needle 80 around which a balloon extension or compressible member 250 is fitted. The balloon extension 250 holds a volume of fluid for the positive flushing feature as described in detail below. Positioned above the balloon extension 250 is a compression plate 260, which acts to press the fluid out of the balloon extension 250 as the needle assembly is moved from the insertion position to the protection position. It should be appreciated that although a balloon extension is illustrated, many possibilities exist for a collapsible or compressible member that could contain within it a volume of fluid and which would collapse upon pressure from an external source. In addition, it should be noted that balloon extension 250 could be made of various materials (for example, silicone or polyurethane), which have the desired properties of ruggedness, attachability and collapsibility so that any problems associated with bursting or loosening from the needle are avoided.

Figure 23:
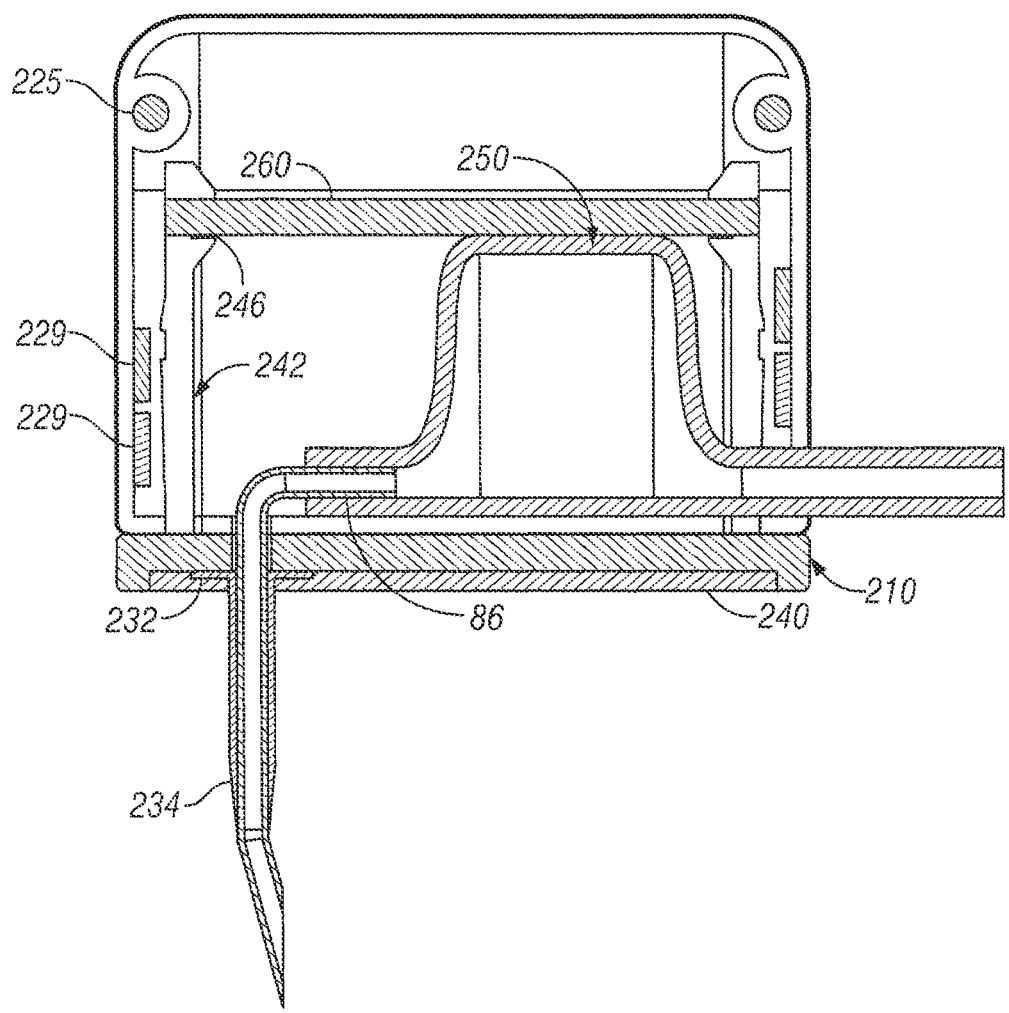
FIG. 23 is side cross-sectional view of the needle assembly of FIG. 18 in the insertion position.

FIG. 23 illustrates, in cross-section, the needle assembly 200 in the insertion position. With reference to this view, the assembly of the needle assembly 200 will be explained, although certainly other manners of assembly are also possible with respect to chemical or mechanical bonds. From this view, the interlocking features of the handle 220 can clearly be seen. As shown in FIG. 22, the right half 224 of the handle 220 has holes 225 in the upper corners thereof to receive pins 227 positioned on the upper corners of the left half of the handle 220, although certainly the holes 225 and pins 227 could be reversed. The handle 220 also includes interlocking tabs 229 positioned on the sides of each half 222, 224 near the lower corners thereof, which are received in corresponding slots on the opposing half. These interlocking features are intended to be one-way or permanent so that convenience of manufacture can be maintained without sacrificing safety, although it is possible that releasable locks would be desired in certain situations. Moreover, while interlocking features have been specifically described, it should be appreciated that various possibilities exist to lock a handle around certain internal parts that would equally be within the scope of the present invention.

Because of the separate halves of the handle 220, assembly of the compression plate 260 can be accomplished without any special tools as the plate 260 is merely slid into the notched sections 246 on each of the four legs 242 of the support structure 240 over the balloon extension 250 after it has been positioned against the lower portion of the handle 220. It should be noted that the handle 220 envelopes the compression plate 260 and the balloon extension 250, but is not attached to the wing base 210. The support structure 240 is chemically bonded to the bottom of the wing base 210 to hold the aforementioned components in place with respect to one another. The balloon extension 250 is bonded to the proximal end 86 of the needle 80 and has a tail 252 extending out of an opening in the back of the handle 220. In the insertion position, the handle 220 is positioned over the central section and has a surface contacting the wing base 210. The balloon extension 250 is positioned between the handle member surface and the compression plate 260. The protection sleeve 230 extends from the wing base 210 to cover a portion of the needle 80 proximal of the distal tip 82 of the needle in the insertion position.

Figure 24:
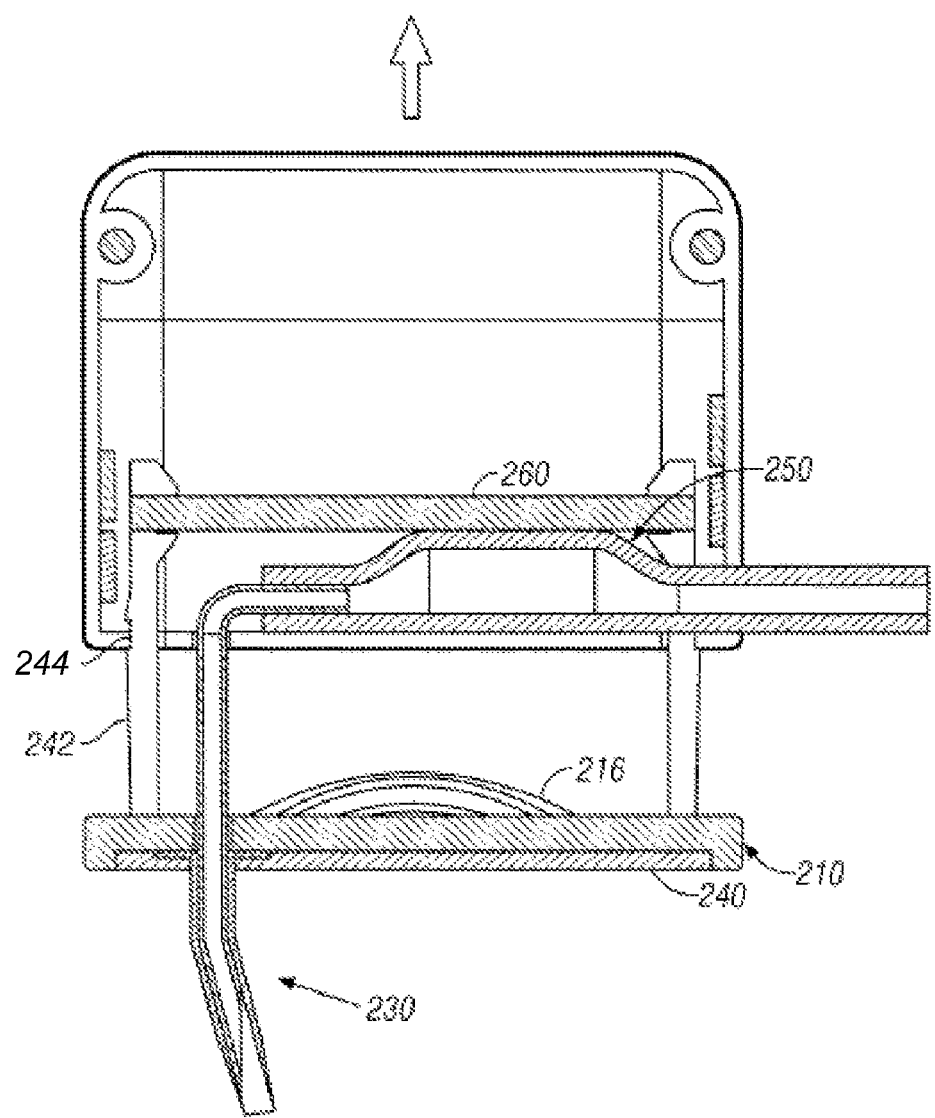
FIG. 24 is a side cross-sectional view of the needle assembly of FIG. 18 in the protection position.

Referring now to FIG. 24, the needle assembly 220 is illustrated in a protection position, showing the interaction between various parts thereof as the needle 80 is withdrawn from a vascular access port (not shown). Similar to embodiments described above, the needle assembly 200 in the insertion position lies on top of a patient's skin, the needle 80 inserted into a vascular access port implanted below the patient's skin. The wing base 210 with the support structure 240 lie flush against the patient's skin. Upon delivery of drug or other medicant to the port, the physician places the index finger and thumb of one hand onto the wing base 210, pressing it against the patient's skin, while grasping the handle 220 with the free hand and pulling it in an upward direction. The handle 220 slides along the legs 242, which remain stationary, being bonded to the wing base 210. The legs 242 are tapered, causing them to bend as the handle 220 is pulled upward, which creates resistance. The resistance is useful in preventing a withdraw that is too quick, which could potentially lead to problems.

The upward action of the handle 220 removes the needle 80 from the vascular access port while simultaneously flushing fluid contained within the balloon extension 250 through the distal needle tip 82, thereby replacing the volume of the needle in the reservoir of the vascular access port with the fluid contained within the balloon extension 250 so that a negative pressure in the vascular access port is averted. A positive flush is created, as shown in FIG. 24, by the action of the compression plate 260 against the balloon extension 250. Specifically, as the handle 220 is pulled upward with respect to the wing base 210, the balloon extension 250, which lies between the base of the handle 220 and the compression plate 260, is compressed as the compression plate 260 remains stationary with respect to the handle 220. More particularly, the compression plate 260 is held in place by the legs of the support structure 240 and is not attached to the handle 220, so that movement of the handle 220 causes the compression of the balloon extension 250.

It should be noted that while a compression plate is described, the present invention would also encompass an embodiment where the compression of the compressible member, such as balloon extension 250, takes place via configurations of the internal portions of the handle or via configurations of the support structure that reaches into the handle. Alternatively, other housing configurations could be imagined within the scope of the present invention that would cause compression of the compressible member upon relative movement between the housing and a base.

Simultaneous to the positive flush taking place, the needle assembly 200 locks into a safety position in two respects. First, the needle tip 82 enters the protection sleeve 230 as the handle 220 is moved upward with respect to the wing base 210. When the handle 220 reaches the position of the first notched section 244 of the legs 242 of the support section 240, the lower portion of the handle 220 locks into place, snapping audibly in the process to provide a positive indication to the physician to cease withdraw. This is the primary locking mechanism for needle assembly 200. Due to the locking interaction between the handle and the legs 242 of the support section 240, the balloon extension 250 is prevented from expanding upon release, which would cause backflow. At this locked position, the needle tip 82 is fully within the protection sleeve 230, the tip coming into contact with the inner surface thereof, which prevents movement out of the sleeve. This secondary locking mechanism ensures that the needle tip 82 is completely covered by the protection sleeve 230 to avoid accidental needle sticks.

The present invention has been described above in terms of certain preferred embodiments so that an understanding of the present invention can be conveyed. However, there are many alternative arrangements for a positive flush mechanism not specifically described herein but with which the present invention is applicable. Although specific features have been provided, the safety needle with positive flush device of the present invention would equally be embodied by other configurations not specifically recited herein. The scope of the present invention should therefore not be limited by the embodiments illustrated, but rather it should be understood that the present invention has wide applicability with respect to a positive flush system generally. All modifications, variations, or equivalent elements and implementations that are within the scope of the appended claims should therefore be considered within the scope of the invention.

What is claimed is:

1. A safety needle device, comprising:
a base member including first and second wing sections extending from opposite sides of a central section, a plurality of legs angularly extending from the central section, the legs cooperating to hold a compression plate therebetween;
a handle member positioned over the central section and having a surface contacting the base member in a device insertion position;
a compressible member positioned between the handle member surface and the compression plate, the compressible member coupled to a proximal end of a needle, wherein movement of the handle member away from the base member collapses the compressible member to flush a volume of fluid contained therein through a distal tip of the needle.

2. The safety needle device according to claim 1, wherein the distal tip of the needle is a non-coring tip.

3. The safety needle device according to claim 2, wherein the proximal end of the needle is angularly positioned relative to a needle shank connecting the proximal end of the needle to the distal tip of the needle.

4. The safety needle device according to claim 1, wherein the first and second wing sections include gripping surfaces.

5. The safety needle device according to claim 1, wherein the base member includes a support structure coupled to the legs, the legs extending at about a 90 degree angle from the support structure.

6. The safety needle device according to claim 1, wherein each of the legs includes a first notched section receiving a portion of the handle member in a device locked position.

7. The safety needle device according to claim 6, wherein each of the legs includes a second notched section receiving a portion of the compression plate therein.

8. The safety needle device according to claim 1, further comprising a protection sleeve bonded to the base member and extending from the base member to cover a portion of the needle proximal of the distal tip of the needle in the device insertion position.

9. The safety needle device according to claim 8, wherein protection sleeve includes material properties to prevent penetration by the distal tip of the needle, a distal end of the protection sleeve having a tapered configuration.

10. The safety needle device according to claim 9, wherein the protection sleeve covers the distal tip of the needle in a device locked position.

11. The safety needle device according to claim 1, wherein the handle member comprises a first half and a second half that permanently couple together around the legs and compressible member.

12. The safety needle device according to claim 1, wherein an angle formed between the legs and base member is about 90 degrees, the handle member surface including openings in which the legs are positioned.

13. The safety needle device according to claim 12, wherein the legs are tapered to create resistance for the movement of the handle member away from the base member.

14. The safety needle device according to claim 1, wherein the compressible member includes a tail extending through an opening in the handle member, the tail fluidly coupled to a fluid source.

15. A method of supplying fluid to a vascular access port, comprising:
providing the safety needle device according to claim 1;
inserting the distal tip of the needle through a patient's skin and into a vascular access port;
delivering fluid first through the compressible member and then through the needle; and
removing the needle from the vascular access port by holding the base member against the patient's skin and moving the handle member away from the base member, a portion of the volume of fluid in the collapsible member flushing into the vascular access port to substantially replace a volume of the needle.

* * * * *